(12) United States Patent
Tu et al.

(10) Patent No.: US 10,076,251 B2
(45) Date of Patent: Sep. 18, 2018

(54) PHYSIOLOGY SIGNAL SENSING DEVICE

(71) Applicant: Maisense Inc., Zhubei, Hsinchu County (TW)

(72) Inventors: Tse-Yi Tu, Zhubei (TW); Paul C. P. Chao, Zhubei (TW); Yung-Pin Lee, Zhubei (TW)

(73) Assignee: Maisense Inc., Zhubei, Hsinchu County (TW)

( * ) Notice: Subject to any disclaimer, the term of this patent is extended or adjusted under 35 U.S.C. 154(b) by 925 days.

(21) Appl. No.: 14/096,478

(22) Filed: Dec. 4, 2013

(65) Prior Publication Data
US 2014/0296734 A1  Oct. 2, 2014

(30) Foreign Application Priority Data

Apr. 1, 2013  (TW) .............................. 102111641 A

(51) Int. Cl.
  *A61B 5/05*  (2006.01)
  *A61B 5/02*  (2006.01)
  *A61B 5/00*  (2006.01)
  *A61B 5/024*  (2006.01)

(52) U.S. Cl.
  CPC ............ *A61B 5/02* (2013.01); *A61B 5/02438* (2013.01); *A61B 5/681* (2013.01); *A61B 5/6824* (2013.01); *A61B 5/6831* (2013.01); *A61B 2562/0261* (2013.01)

(58) Field of Classification Search
None
See application file for complete search history.

(56) References Cited

U.S. PATENT DOCUMENTS

| 4,561,447 A | 12/1985 | Kawamura et al. |
| 5,406,952 A * | 4/1995 | Barnes ................... A61B 5/021 600/485 |
| 2004/0243009 A1 | 12/2004 | Tanaka et al. |
| 2005/0107658 A1* | 5/2005 | Brockway ............. A61M 1/122 600/16 |
| 2007/0112274 A1* | 5/2007 | Heitzmann .......... A61B 5/0002 600/485 |

(Continued)

FOREIGN PATENT DOCUMENTS

CN   1572237 A   2/2005
JP   2003-532478   11/2003

(Continued)

OTHER PUBLICATIONS

European Search Report dated Aug. 18, 2014, in corresponding EP Patent Application No. 14159185.9.

(Continued)

*Primary Examiner* — Etsub Berhanu
(74) *Attorney, Agent, or Firm* — Muncy, Geissler, Olds & Lowe, P.C.

(57) ABSTRACT

A physiology signal sensing device includes an elastic pad and a strain sensor element. The elastic pad is used for contact with a human body, and corresponds a blood vessel of the human body. The strain sensor element is disposed in the elastic pad and includes a conductive element. The conductive element deforms according to the vibration of the blood vessel, and the resistance value of the conductive element varies according to the strain of the conductive element.

7 Claims, 6 Drawing Sheets

(56) References Cited

U.S. PATENT DOCUMENTS

2007/0287923 A1   12/2007  Adkins et al.
2009/0177096 A1    7/2009  Kim
2011/0152694 A1    6/2011  Shimoyama et al.
2012/0150047 A1*  6/2012  Terumoto ........... A61B 5/02427
                                                                600/479

FOREIGN PATENT DOCUMENTS

WO       WO 01/85024 A1    11/2001
WO       WO 2009/109903 A1  9/2009

OTHER PUBLICATIONS

EP Search Report dated Jan. 14, 2015 from corresponding EP Appl No. 14159185.9.

* cited by examiner

PHYSIOLOGY SIGNAL SENSING DEVICE

CROSS-REFERENCE TO RELATED APPLICATIONS

This Application claims priority of Taiwan Patent Application No. 102111641, filed on Apr. 1, 2013, the entirety of which is incorporated by reference herein.

BACKGROUND OF THE INVENTION

Field of the Invention

The present invention relates to a sensing device, and in particular, to a physiology signal sensing device.

Description of the Related Art

In general, conventional mechanical blood pressure monitors have pumping cuffs to apply pressure on users. However, the pressure generated by the pumping cuff is not comfortable for users, and thus, the blood pressure monitors may not be continually used for a long time. Moreover, the blood pressure monitors are not be carried easily by a user because of the large size and the heavy weight of the pumping cuff.

Otherwise, an electronic type of conventional blood pressure monitors is available, which utilizes piezoelectric sensors for detecting. The piezoelectric sensors have the advantage of being small size, and continually used for a long time is available. However, the cost of the piezoelectric sensor is high, and the blood pressure detected by the blood pressure monitor is not accurate because the current generated by the piezoelectric sensor is unstable. Thus, the piezoelectric sensor is usually used for detecting heart rates only.

BRIEF SUMMARY OF THE INVENTION

To solve the problems of the prior art, the object of the present disclosure is to provide a physiology signal sensing device that is accurate with a lower cost. In addition, the physiology signal sensing device may be continually used for a long time and be easily carried by user.

The present disclosure provides a physiology signal sensing device including an elastic pad and a strain sensor element. The elastic pad is for contact with a human body and corresponds to a blood vessel of the human body. The strain sensor element includes a sensing body and a conductive element. The sensing body is disposed in the elastic pad, and the conductive element disposed on the sensing body has a variable resistance value. The conductive element deforms according to a vibration of the blood vessel, and the resistance value of the conductive element varies according to the strain of the conductive element.

The present disclosure provides a physiology signal sensing device including an elastic pad, an elastic strip, a strain sensor element, and a processing module. The elastic pad is for contact with a human body and corresponds to a blood vessel of the human body. The elastic strip is disposed in the elastic pad. The strain sensor element is disposed on the elastic strip, and includes a sensing body and a conductive element. The conductive element disposed on the sensing body has a variable resistance value. The processing module is electrically connected to the conductive element.

The conductive element deforms according to a vibration of the blood vessel, and the resistance value of the conductive element varies according to the strain of the conductive element. The processing module generates a physiology signal according to the resistance value.

In conclusion, the physiology signal sensing device of the present disclosure generates a physiology signal according to changes of the resistance value, which depends on the strain of the conductive element, and thus, an accurate detection is provided and the manufacturing cost is decreased. Moreover, the physiology signal sensing device of the present disclosure excludes a pumping cuff. Thus, the physiology signal sensing device may be continually used for a long time and be easily carried by a user, and the size thereof is small and the weight thereof is light.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1:
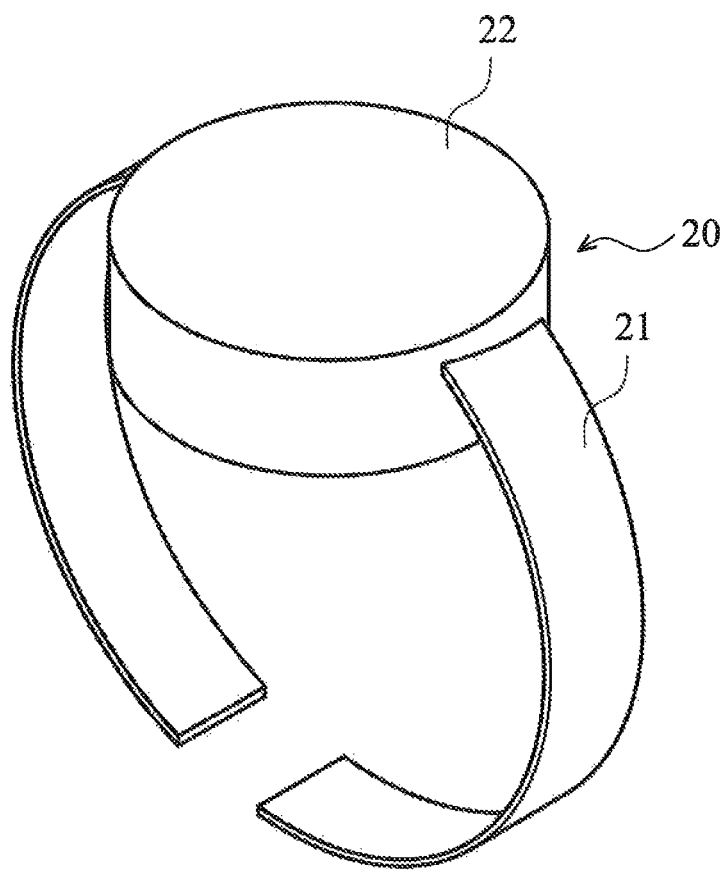
FIG. 1 is a perspective view of a physiology signal sensing device according to a first embodiment of the present disclosure.

The shape, size, or thickness in the drawings may not be drawn to scale or simplified for clarity purpose; rather, these drawings are merely intended for illustration.

Figure 2:
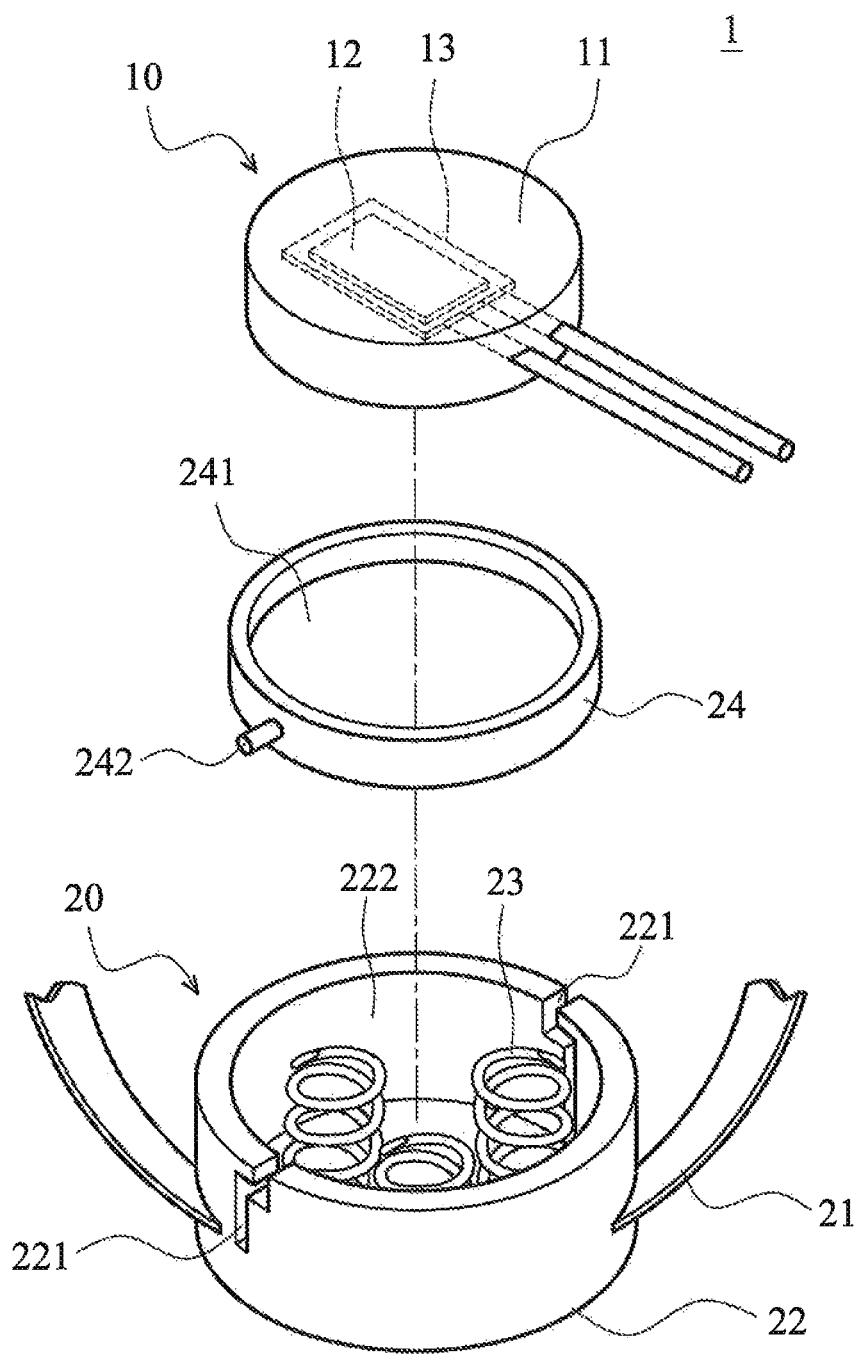
FIG. 2 is an exploded view of the physiology signal sensing device according to the first embodiment of the present disclosure.
Figure 3:
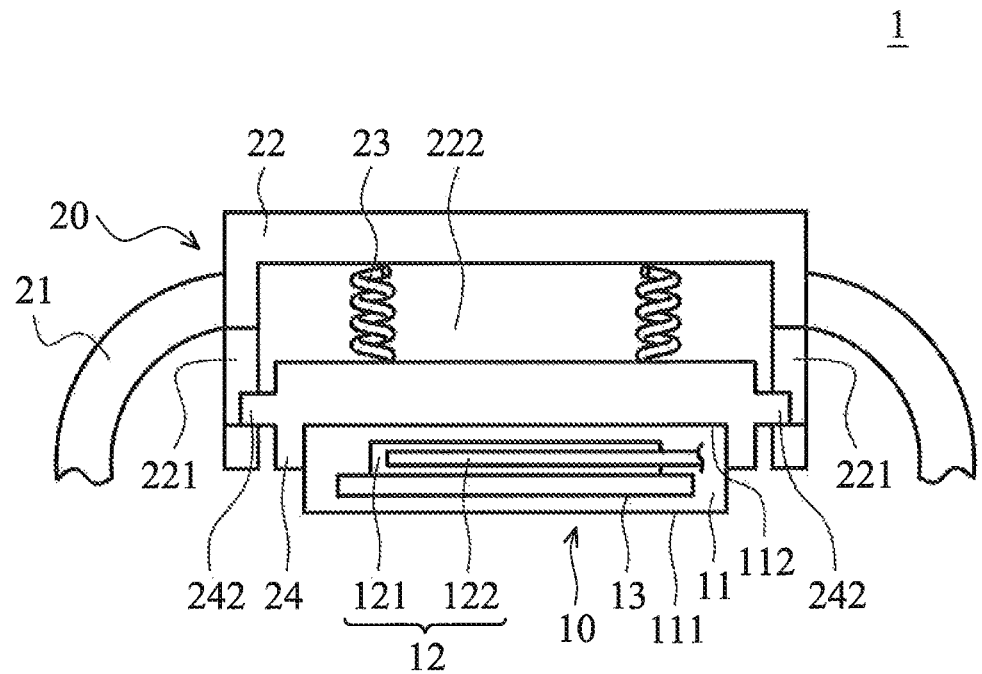
FIG. 3 is a cross-sectional view of the physiology signal sensing device according to the first embodiment of the present disclosure.

FIG. 1 is a perspective view of a physiology signal sensing device 1 according to a first embodiment of the present disclosure. FIG. 2 is an exploded view of the physiology signal sensing device 1 according to the first embodiment of the present disclosure. FIG. 3 is a cross-sectional view of the physiology signal sensing device 1 according to the first embodiment of the present disclosure. The physiology signal sensing device 1 is for detecting physiology signals of users to obtain physiology information, such as blood pressure, pulse rate, and heart rate.

The physiology signal sensing device 1 includes a sensor 10 and a pressing element 20. The sensor 10 is disposed on the pressing element 20. The sensor 10 may contact with a human body and correspond to a blood vessel of the human body. The pressing element 20 presses the sensor 10 to increase the sensitivity of the sensor 10. The sensor 10 deforms according to the vibration of the blood vessel.

The sensor 10 includes an elastic pad 11, a strain sensor element 12, and an elastic strip 13. The elastic pad 11 includes soft rubber, soft plastic, soft polymer, liquid silicone rubber, or polydimethylsiloxane (PDMS). The hardness of Shore A of the elastic pad 11 may be from 0 HA to 50 HA, or from 20 HA to 50 HA. The thickness of the elastic pad 11 is from 0.01 mm to 20 mm. In the embodiment, the elastic pad 11 includes polydimethylsiloxane, and the thickness of the elastic pad 11 is 7 mm.

The strain sensor element 12 is disposed in the elastic pad 11, and includes a sensing body 121 and a conductive element 122. The sensing body 121 may be a sheet structure and may be an insulated material, such as a rubber or a soft plastic. The conductive element 122 may be a sheet structure or a wire disposed in the sensing body 121. In another embodiment, the conductive element 122 is disposed on a surface of the sensing body 121.

The elastic strip 13 is disposed in the elastic pad 11 and disposed on the sensing body 121. The elastic strip 13 may be located between a contact surface 111 of the elastic pad 11 and the sensing body 121, and is disposed about 0.01 mm to 10 mm away from the contact surface. In the embodiment, the distance is about 2 mm. The elastic strip 13 may be parallel to the sensing body 121 and the conductive element 122. The area of the elastic strip 13 is greater than the area of sensing body 121. The elastic strip 13 includes metal material, such as carbon steel. The tensile strength of the elastic strip 13 is from 600 Mpa to 1000 Mpa, the yield strength thereof is from 350 Mpa to 500 Mpa, the brinell hardness thereof is about 248, and the thickness thereof is from 0.1 um to 500 um.

The pressing element 20 is disposed on a pressure surface 112 and a side surface of the elastic pad 11. The pressure surface 112 and the contact surface 111 are respectively located at two opposite sides of the elastic pad 11. The pressing element 20 includes a retaining belt 21, a housing 22, and a plurality of elastic elements 23. The retaining belt 21 may be elastic material, such as an elastic fabric. In another embodiment, the retaining belt 21 may include two belt structures hooked to each other, such as a watch belt.

The housing 22 is disposed on the retaining belt 21. In the embodiment, two ends of retaining belt 21 are fixed on two opposite sides of the housing 22. The housing 22 may include two retaining holes 221 and a receiving groove 222. The retaining hole 221 is located at a sidewall of the housing 22, and communicates with the receiving groove 222. The elastic element 23 may be a spring disposed in the receiving groove 222.

The cover 24 is located between the elastic element 23 and the elastic pad 11, and located in the receiving groove 222 of the housing 22. The cover 24 has a holding groove 241 and two retaining protrusion 242 communicating with the holding groove 241. The pressure surface 112 of the elastic pad 11 may be fixed in the holding groove 241. The retaining protrusion 242 is located in the retaining hole 221 to limit the cover 24 from moving in the receiving groove 222.

The pressing element 20 may be a watch like structure, and thus, the physiology signal sensing device 1 may be fixed on the wrist of a user by the retaining belt 21. The cover 24 presses the elastic pad 11 by the elastic element 23 to make the sensor 10 of the elastic pad 11 stably attach on the skin of the human body. Thus, the sensor 10 may continually process detection of a user for a long period of time.

In another embodiment, the elastic element 23 includes elastic material, such as rubber or soft plastic, and the cover 24 may be excluded. The two opposite sides of the elastic element 23 are respectively fixed on the receiving groove 222 and the pressure surface 112 of the elastic pad 11.

Figure 4:
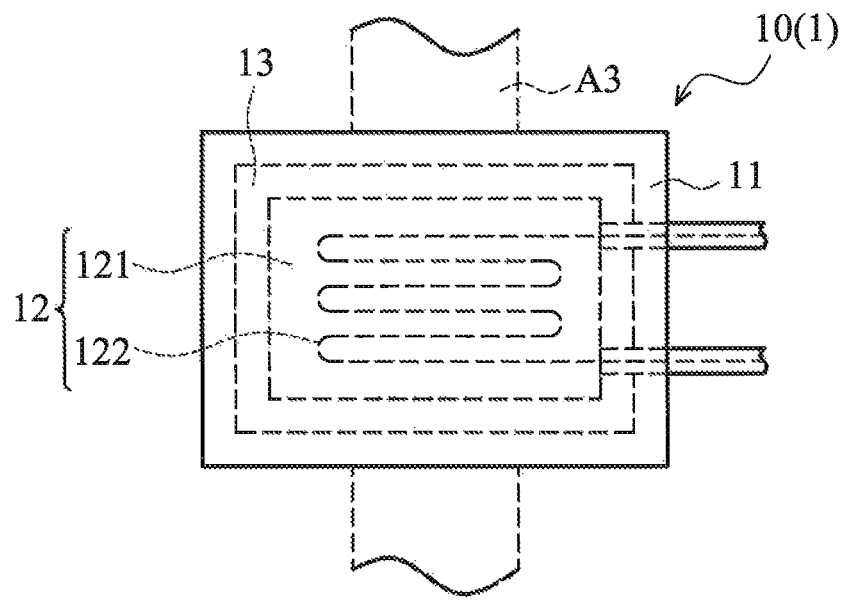
FIG. 4 is a top view of the physiology signal sensing device of the present disclosure during a detection process.
Figure 5:
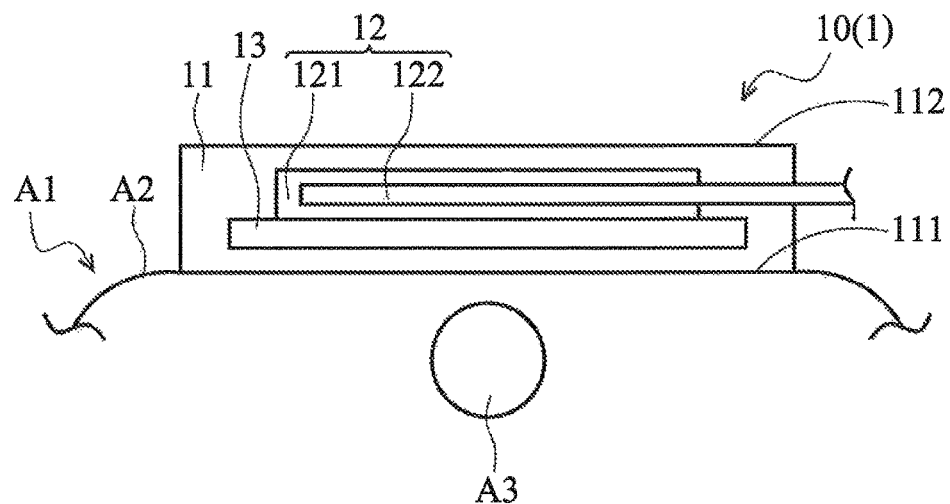
FIGS. 5 and 6 are cross-sectional views of the physiology signal sensing device of the present disclosure during a detection process.
Figure 6:
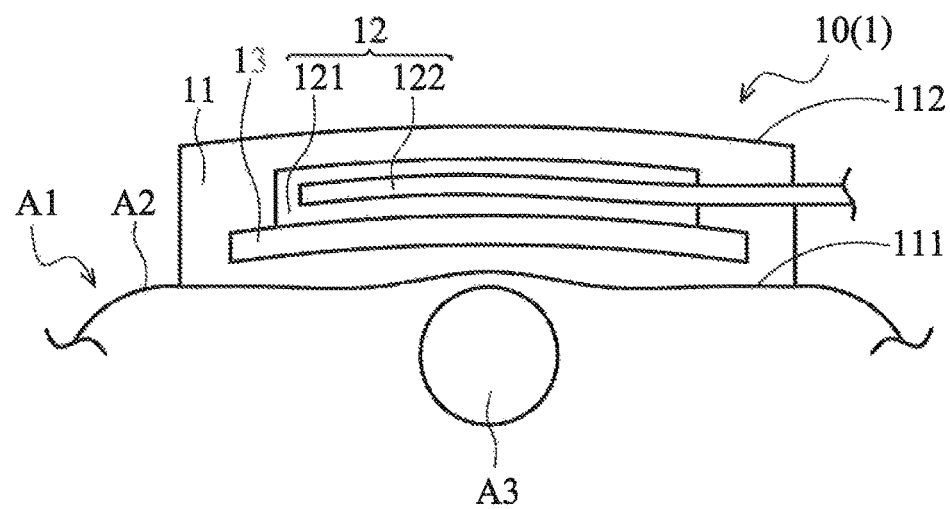

FIG. 4 is a top view of the physiology signal sensing device 1 of the present disclosure during a detection process. FIGS. 5 and 6 are cross-sectional views of the physiology signal sensing device 1 of the present disclosure during a detection process. For the purpose of simplification and clarity, the pressing element 20 is not drawn on FIGS. 4 to 6.

When the user uses the physiology signal sensing device 1, the physiology signal sensing device 1 may be fixed on the human body A1 (such as wrist), and the elastic pad 11 contacts with the skin A2 of the human body A1 and corresponds to a blood vessel A3 of the human body A1. Namely, the elastic pad 11, the strain sensor element 12, and the elastic strip 13 are located above the blood vessel A3 and adjacent to blood vessel A3. The blood vessel A3 may be an artery, such as a radial artery.

Since the material of the elastic pad 11 is soft, it is comfortable for a user to carry with, and decreases the noise signal generated by the vibration of the blood vessel A3. The length of the elastic strip 13 is greater than (double of the size in the embodiment) the diameter of the blood vessel A3 and the material of the elastic strip 13 is elastic metal, and thus, the strain of the elastic strip 13 may accurately match to a minor vibration of the blood vessel A3. Because the strain sensor element 12 is attached to the elastic strip 13, the curvatures of the strain sensor element 12 and the elastic strip 13 are the same.

The conductive element 122 within the strain sensor element 12 may be a wire, curved inside of the sensing body 121. As shown in FIG. 4, the conductive element 122 may include a plurality of straight sections parallel to each other. The straight sections may be substantially perpendicular to the blood vessel A3 to obtain detection.

As shown in FIG. 5, the blood vessel A3 constricts in the diastolic phase of the cardiac cycle. The elastic pad 11, the strain sensor element 12, and the elastic strip 13 are not bent, or bent according to the curvature of the skin A2. As shown in FIG. 6, the blood vessel A3 dilates in the phase systolic of the cardiac cycle. The skin A2 is curved according to the vibration of the blood vessel A3.

The elastic pad 11 and the elastic strip 13 continually deforms according to the degree of the vibration of the skin A2 and the blood vessel A3, and the strain sensor element 12 continually deforms according to the strain of the elastic strip 13. Thus, the strain of the strain sensor element 12 corresponds to the degree of the vibration of the blood vessel A3 and the skin A2. Also, the elastic pad 11, the strain sensor element 12, the conductive element 122, and the elastic strip 13 disposed above the blood vessel A3 have a greater curvature according to the diastolic blood vessel A3.

Since, the conductive element 122 is bent or curved, the length and/or the curvature of the conductive element 122 changes, and thus, resistance value of the conductive element 122 changes. Namely, the length and/or the curvature of the conductive element 122 continually changes with each of the systolic or diastolic vibrations of the blood vessel A3, and the resistance value continually changes according to the changing of the length and/or the curvature of the conductive element 122. Therefore, the resistance value of the conductive element 122 according to the vibration of the blood vessel A3, and the frequency of the change of the resistance value corresponds to the heart rate of the user.

Since the present disclosure utilizes the strain of the sensor 10 to detect, it is possible to continually detect the physiology signal. Moreover, the sensor 10 has the advantages of being small in size and having a light weight, and thus, the sensor 10 can be easily carried by a user.

Figure 7:
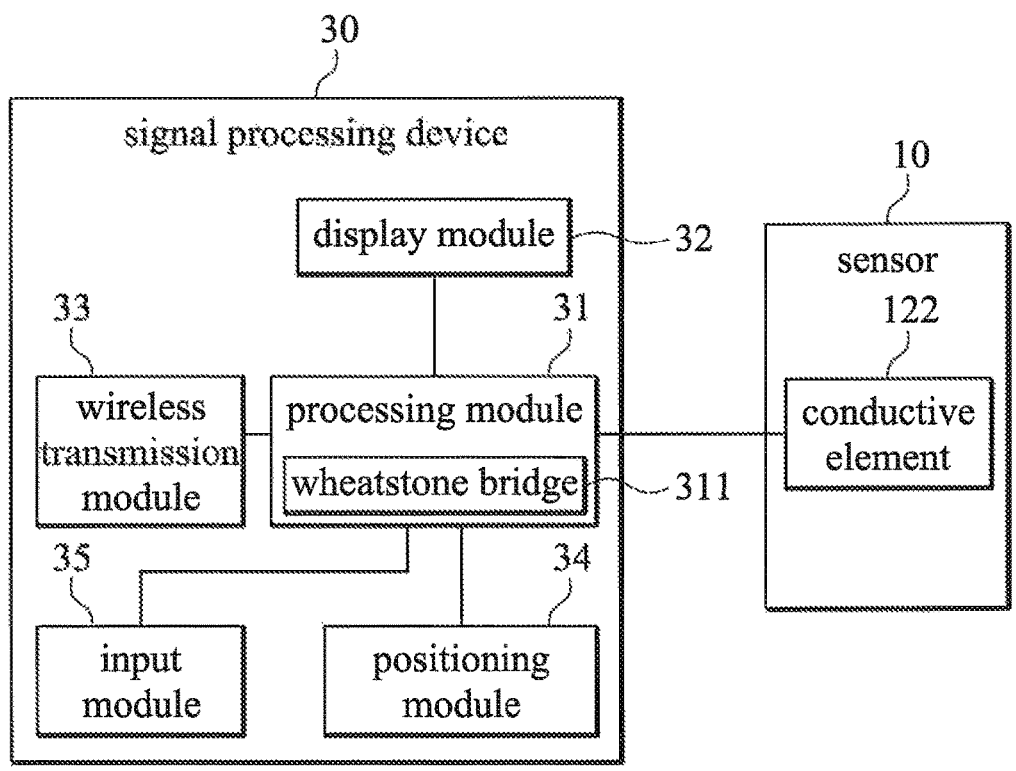
FIG. 7 is a system diagram of the physiology signal sensing device according to a first embodiment of the present disclosure.

FIG. 7 is a system diagram of the physiology signal sensing device 1 according to a first embodiment of the present disclosure. The physiology signal sensing device 1 further includes a signal processing device 30 electrically connected to the sensor 10 and generating the physiology signal according to the strain of the sensor 10. The signal processing device 30 is selectively disposed on the retaining belt 21. The signal processing device 30 includes a processing module 31, a display module 32, a wireless transmission module 33, a positioning module 34, and an input module 35. The processing module 31 is electrically connected to the display module 32, the wireless transmission module 33, the positioning module 34, the input module 35, and the conductive element 122.

The processing module 31 detects and records the resistance value according to the strain, such as the change of the length and the curvature, of the element 122, and generates a physiology signal according to the record. In the embodiment, the processing module 31 includes a wheatstone bridge 311. The wheatstone bridge 311 is electrically connected to the conductive element 122, and the processing module 31 utilizes the wheatstone bridge 311 to detect the resistance value of the conductive element 122. The physiology signal may be a wave-shaped signal according to the vibration of the blood vessel A3 in real-time, and thus, the processing module 31 may calculate the physiology information, such as pulse, blood pressure, and heart rate of the user according to the physiology signal. The processing module 31 may control the display module 32 to display the physiology signal and the physiology information.

The positioning module 34 receives the coordinate signal and transmits it to the processing module 31. The processing module 31 controls the wireless transmission module 33 to transmit a wireless signal to a remote electronic device, such as a mobile phone or computer, according to the physiology signal. Thus, the health condition of a user may be analyzed or tracked by doctors or family of the user. If the health condition of the user gets worse, the position of the user can be known and appropriate actions may be executed.

The input module 35 may be a button operated to switch the information, such as the blood pressure, pulse, or heart rate of the user, displayed by the display module 32.

In another embodiment, the signal processing device 30 may just include the processing module 31 and the wireless transmission module 33 to further decrease the size and the weight of the physiology signal sensing device 1.

Figure 8:
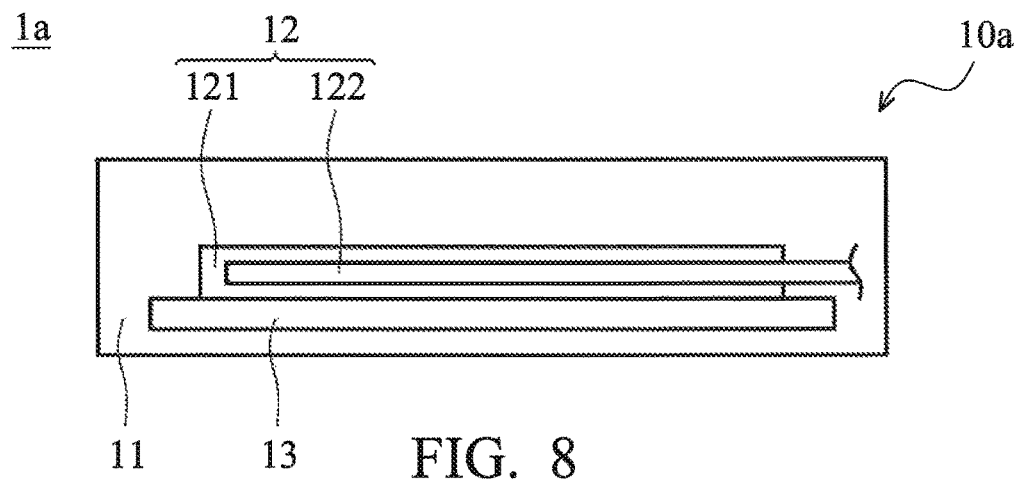
FIG. 8 is a cross-sectional view of a physiology signal sensing device according to a second embodiment of the present disclosure.

FIG. 8 is a cross-sectional view of a physiology signal sensing device 1a according to a second embodiment of the present disclosure. The physiology signal sensing device 1a may exclude the pressing element 20 of the first embodiment. The sensor 10a may be adhered to the human body A1 (as shown in FIGS. 5 and 6) or retained on the human body A1 by a hand of a user. The sensor 10a may provide pressure by the gravity thereof on the human body A1. The elastic strip 13 may be selectively excluded to further decrease the size and the weight of the physiology signal sensing device 1a.

Figure 9:
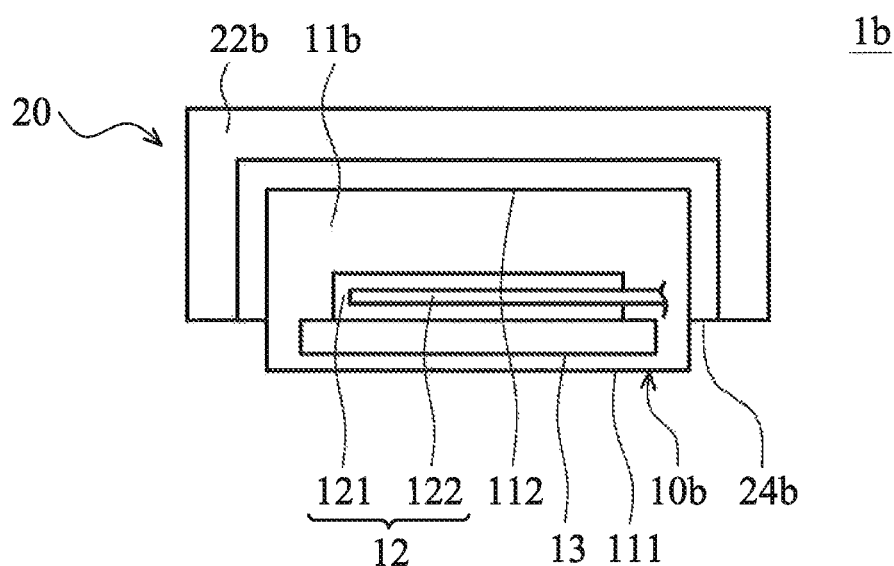
FIG. 9 is a cross-sectional view of a physiology signal sensing device according to a third embodiment of the present disclosure.

FIG. 9 is across-sectional view of a physiology signal sensing device 1b according to a third embodiment of the present disclosure. The differences between the third embodiment and the first embodiment are described as follows. The third embodiment excludes the elastic element 23 of the first embodiment. The housing 22b may exclude the retaining hole 221 of the first embodiment, and the cover 24b may exclude the retaining protrusion 242 of the first embodiment. The distance between the strain sensor element 12 of the sensor 10b and the pressure surface 112 of the elastic pad 11b is greater than the first embodiment, and the pressure of the elastic pad 11b to the skin A2 (as shown in FIGS. 5 and 6) is increased due to the weight of the housing 22b and the elastic pad 11b.

In the embodiment, the retaining belt 21 may be excluded. The physiology signal sensing device 1b may be disposed on another device, such as a pen or a mobile phone. The user may directly or indirectly apply a force to the physiology signal sensing device 1b to place the physiology signal sensing device 1b on the human body. In addition, in the disclosed embodiment, the retaining belt 21 may be excluded, too. Moreover, in the embodiment, the cover 24a may be excluded, and the pressure surface 112 of the elastic pad 11a directly contacts with the housing 22a.

In conclusion, the physiology signal sensing device of the present disclosure generates a physiology signal according to changes of the resistance value, which depends on the strain of the conductive element, and thus, accurate detection is provided and the manufacturing cost is decreased. Moreover, the physiology signal sensing device of the present disclosure excludes a pumping cuff. Thus, the physiology signal sensing device may be continually used for a long time and be easily carried by a user, and the size thereof is small and the weight thereof is light.

The disclosed features may be combined, modified, or replaced in any suitable manner in one or more disclosed embodiments, but are not limited to any particular embodiments.

While the invention has been described by way of example and in terms of preferred embodiment, it is to be understood that the invention is not limited thereto. On the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A physiology signal sensing device, comprising:
   an elastic pad used for contact with a human body and which deforms according to a vibration of a blood vessel of the human body;
   an elastic strip, embedded into and in direct contact with the elastic pad, wherein the elastic strip deforms according to the vibration of the blood vessel;
   a strain sensor element, disposed on the elastic strip, comprising:
      a sensing body embedded into and in direct contact with the elastic pad; and
      a conductive element, embedded into and in direct contact with the sensing body, having a variable resistance value, and
   a pressing element, disposed on the elastic pad configured to press the elastic pad, comprising:
      a cover disposed on the elastic pad;
      a housing disposed on the cover; and
      an elastic element, located between the housing and the cover;
   wherein the conductive element deforms according to the vibration of the blood vessel, the strain of the conductive element corresponds to the elastic strip, and the resistance value of the conductive element varies according to the strain of the conductive element.

2. The physiology signal sensing device as claimed in claim 1, wherein a curvature of the conductive element corresponds to the vibration of the blood vessel.

3. The physiology signal sensing device as claimed in claim 1, further comprising:

a processing module electrically connected to the conductive element, wherein the processing module generates a physiology signal according to the resistance value, wherein the processing module further comprises a wheatstone bridge electrically connected to the conductive element, and the processing module detects the resistance value by using the wheatstone bridge; and a display module electrically connected to the processing module, wherein the processing module controls the display module to display the physiology signal.

4. The physiology signal sensing device as claimed in claim 3, further comprising a wireless transmission module electrically connected to the processing module, wherein the processing module controls the wireless transmission module to transmit a wireless signal according to the physiology signal.

5. The physiology signal sensing device as claimed in claim 1, wherein the pressing element further comprises a retaining belt disposed on the housing.

6. A physiology signal sensing device, comprising:

an elastic pad used for contact with a human body and which deforms according to a vibration of a blood vessel of the human body;

an elastic strip embedded into and in direct contact with the elastic pad, wherein the elastic strip deforms according to the vibration of the blood vessel;

a strain sensor element, disposed on the elastic strip, comprising:
  a sensing body embedded into and in direct contact with the elastic pad; and
  a conductive element, embedded into and in direct contact with the sensing body, having a variable resistance value;

a pressing element, disposed on the elastic pad configured to press the elastic pad, comprising:
  a cover disposed on the elastic pad;
  a housing disposed on the cover; and
  an elastic element, located between the housing and the cover; and a processing module electrically connected to the conductive element, wherein the conductive element deforms according to the vibration of the blood vessel, and the strain of the conductive element corresponds to the elastic strip, and the resistance value of the conductive element varies according to the strain of the conductive element, and wherein the processing module generates a physiology signal according to the resistance value.

7. The physiology signal sensing device as claimed in claim 6, wherein the processing module further comprises a wheatstone bridge electrically connected to the conductive element, and the processing module detects the resistance value by using the wheatstone bridge.

* * * * *